United States Patent
Elsen et al.

(10) Patent No.: US 10,426,716 B2
(45) Date of Patent: *Oct. 1, 2019

(54) COMPOSITIONS AND METHODS FOR IMPROVING COLOR DEPOSIT AND DURABILITY OF COLOR IN ARTIFICIALLY COLORED HAIR

(71) Applicant: L'OREAL, Paris (FR)

(72) Inventors: Andrea Elsen, Linden, NJ (US); Nghi Van Nguyen, Edison, NJ (US); Jim Singer, South Orange, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/691,004

(22) Filed: Aug. 30, 2017

(65) Prior Publication Data
US 2019/0060195 A1   Feb. 28, 2019

(51) Int. Cl.
| | | |
|---|---|---|
| *A61Q 5/10* | (2006.01) | |
| *A61K 8/365* | (2006.01) | |
| *A61K 8/20* | (2006.01) | |
| *A61K 8/22* | (2006.01) | |
| *A61K 8/27* | (2006.01) | |

(52) U.S. Cl.
CPC ............ *A61K 8/365* (2013.01); *A61K 8/20* (2013.01); *A61K 8/22* (2013.01); *A61K 8/27* (2013.01); *A61Q 5/10* (2013.01); *A61K 2800/88* (2013.01)

(58) Field of Classification Search
CPC ... A61Q 5/10; A61K 8/20; A61K 8/27; A61K 8/365; A61K 8/22; A61K 2800/88
See application file for complete search history.

(56) References Cited

U.S. PATENT DOCUMENTS

| | | | |
|---|---|---|---|
| 5,006,127 A | 4/1991 | Lorenz | |
| 5,346,509 A | 9/1994 | Prota | |
| 5,368,610 A | 11/1994 | Wenke | |
| 5,525,123 A | 6/1996 | Lorenz | |
| 5,708,151 A | 1/1998 | Mockli | |
| 5,961,667 A * | 10/1999 | Doehling | A61Q 5/10 8/406 |
| 6,616,707 B2 | 9/2003 | Lorenz | |
| 7,713,310 B2 | 5/2010 | Lalleman | |
| 8,337,570 B2 | 12/2012 | Schafer | |
| 8,883,127 B2 | 11/2014 | Pratt | |
| 9,375,393 B2 | 6/2016 | Lalleman | |
| 2002/0189031 A1 | 12/2002 | Dousse | |
| 2005/0142090 A1 | 6/2005 | Watanabe | |
| 2008/0134449 A1 | 6/2008 | Lalleman | |
| 2008/0229521 A1 | 9/2008 | Lalleman | |
| 2008/0260672 A1 | 10/2008 | Oshimura | |
| 2013/0219633 A1 * | 8/2013 | Sabelle | A61K 8/347 8/424 |
| 2013/0340783 A1 | 12/2013 | Lalleman | |
| 2013/0340784 A1 | 12/2013 | Lalleman | |
| 2015/0265525 A1 | 9/2015 | Benn | |
| 2017/0165160 A1 | 6/2017 | Krohn | |

FOREIGN PATENT DOCUMENTS

| | | | |
|---|---|---|---|
| DE | 19904291 A1 | 8/2000 | |
| EP | 0714954 A2 | 6/1996 | |
| EP | 1923042 A2 | 5/2008 | |
| EP | 2438900 A1 | 4/2012 | |
| FR | 2996125 A1 | 4/2014 | |
| WO | 95/01772 A2 | 1/1995 | |
| WO | 95/15144 A2 | 6/1995 | |
| WO | 2011/045404 A2 | 4/2011 | |
| WO | 2012/084867 A2 | 6/2012 | |
| WO | WO 2012/175720 A1 * | 12/2012 | ............ A61Q 5/10 |
| WO | WO-2017/197117 A1 | 11/2017 | |

OTHER PUBLICATIONS

International Search Report and Written Opinion dated Jan. 3, 2019 for corresponding PCT Application No. PCT/US2018/048500.
U.S. Appl. No. 15/691,043, filed Aug. 30, 2017.

* cited by examiner

*Primary Examiner* — Eisa B Elhilo
(74) *Attorney, Agent, or Firm* — Polsinelli PC

(57) ABSTRACT

The present disclosure relates to compositions and methods for improving the quality and durability of color in artificially colored hair. The compositions are hair coloring compositions that employ divalent metal salts of inorganic acids, monovalent or divalent metal salts of organic acids and colorants. Methods are described wherein hair is contacted with the compositions of the present disclosure, resulting in improved artificial color deposition, as well as improved quality and durability of the color in artificially colored hair.

37 Claims, No Drawings

COMPOSITIONS AND METHODS FOR IMPROVING COLOR DEPOSIT AND DURABILITY OF COLOR IN ARTIFICIALLY COLORED HAIR

FIELD OF THE DISCLOSURE

The present disclosure relates to compositions and methods for depositing color and providing color protection to hair, in particular, for improving the quality and durability of color in artificially colored hair.

BACKGROUND

There are many products available for changing the natural color of hair. The process of changing the color of hair can involve either depositing an artificial color onto the hair, which provides a different shade or color to the hair, or lifting the color of the hair, such as for example, from a dark brown shade to a medium brown or a light brown shade. Hair color can be changed using permanent, semi-permanent, or temporary hair coloring products.

Many consumers desire a permanent color change and therefore use products containing permanent dyes. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain ammonia or other alkalizing agents such as monoethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Newly, permanently colored hair usually has a vibrant, shiny, and rich appearance. Unfortunately, however, in just a few short weeks, or in some cases even less, the color begins to fade due to washing, including shampooing, or exposure to environmental conditions. For instance, gorgeous rich brown colors become muddy and dull, beautiful shades of blonde turn brassy, and vibrant reds do not look so vibrant anymore acquiring golden, orange or brownish tonalities not desirable to the consumer. As described herein, the inventors of the instant disclosure have developed composition, methods and kits that improve color deposit onto hair and/or color durability by preventing color fading from hair.

SUMMARY OF THE DISCLOSURE

The present disclosure relates to improving the amount of artificial color deposited onto hair, as well as the quality and durability of the color in artificially colored hair. The methods described herein employ metal salts such as alkaline earth and alkali metal salts in a hair dyeing system. When these metal salts are used in the compositions and methods described herein, color deposit, color quality and color durability are improved.

In one aspect, the invention of the present disclosure is directed to hair coloring compositions containing, in a cosmetically acceptable solvent:
  (a) one or more divalent metal salts of an inorganic acid;
  (b) one or more monovalent or divalent metal salts of an organic acid; and
  (c) one or more colorants chosen from oxidative dye precursors, direct dyes, pigments, and mixtures thereof.

In another aspect, the invention of the present disclosure is directed to hair coloring compositions containing, in a cosmetically acceptable solvent:
  (a) one or more divalent metal salts of an inorganic acid in an amount of greater than 1 to about 20% by weight, based on the total weight of the hair coloring composition;
  wherein the metal salts are chosen from metal salts of halides, metal hydroxides, metal sulfates, metal oxides, and mixtures thereof; and
  wherein the divalent metal is calcium, zinc, iron, nickel, copper, silver, magnesium, strontium, barium, manganese, or cobalt; and
  (b) one or more colorants chosen from oxidative dye precursors, direct dyes, pigments, and mixtures thereof The hair coloring compositions of the present disclosure are capable of being combined with one or more oxidizing agents or developer compositions containing one or more oxidizing agents wherein the oxidizing agents are chosen from peroxides, persulfates, perborates, percarbonates, alkali metal bromates, ferricyanides, laccases, peroxidases, redox enzymes, their salts thereof, and mixtures thereof.

In another aspect, the invention of the present disclosure is directed to ready to use hair dye compositions containing, in a cosmetically acceptable solvent:
  (a) one or more divalent metal salts of an inorganic acid;
  (b) one or more monovalent or divalent metal salts of an organic acid;
  (c) one or more colorants chosen from oxidative dye precursors, direct dyes, pigments, and mixtures thereof; and
  (d) one or more oxidizing agents chosen from peroxides, persulfates, perborates, percarbonates, alkali metal bromates, ferricyanides, laccases, peroxidases, redox enzymes, their salts thereof, and mixtures thereof.

Methods for artificially coloring hair and/or inhibiting the artificial coloring from fading are also described, wherein said methods comprise contacting hair with a ready to use dye composition for a sufficient period of time to achieve a desired color of the hair and/or alteration of the color of hair; wherein the ready to use dye composition is formed from the combination of the hair coloring compositions of the present disclosure with an oxidizing composition containing: (i) one or more oxidizing agents chosen from peroxides, urea peroxide, alkali metal bromates, ferricyanides, peroxygenated salts, perborates, percarbonates, laccases, peroxidases, redox enzymes, and mixtures thereof, and (ii) a cosmetically acceptable solvent selected from water and a water/organic solvent mixture The one or more divalent metal salts of an inorganic acid are chosen from metal halides, metal hydroxides, metal sulfates, metal oxides, and mixtures thereof.

The one or more divalent metal salts of an inorganic acid or of an organic acid are chosen from salts of calcium, zinc, iron, nickel, copper, silver, magnesium, strontium, barium, manganese, cobalt, and mixtures thereof.

The one or more monovalent metal salts of an organic acid are chosen from salts of lithium, sodium, potassium, copper, silver, and mixtures thereof.

The organic acid of the one or more monovalent or divalent metal salts of an organic acid is chosen from C1 to C9 monocarboxylic or di-carboxylic acids, polycarboxylic acids, hydroxy-carboxylic acids, and fatty acids having at least 10 carbon atoms including ascorbic acid, formic acid, acetic acid, glycolic acid, gluconic acid, lactic acid, mandelic acid, oxalic acid, maleic acid, malonic acid, glyoxylic acid, succinic acid, adipic acid, fumaric acid, sebacic acid, including citric acid, tartaric acid, malic acid, 2-hydroxy malonic acid, 2-hydroxyl n-butyl 1,2,4-tricarboxylic acid, glutaric acid, glucaric acid, 2-hydroxy n-butyl 1,3,4-tricarboxylic acid, pyrrolidone carboxylic acid, phenolsulfonic acid, and salicylic acid Finally, the instant disclosure relates to kits comprising the various compositions used to carry out the methods described herein. The kits may be used by hair-care professionals and salons for treating the hair of patrons or the kits may be purchased and used at home directly by consumers.

It is to be understood that both the foregoing general description and the following detailed description are exemplary and explanatory only, and are not restrictive of the disclosure.

Other subjects, characteristics, aspects and advantages of embodiments of the disclosure will emerge even more clearly on reading the description and the various examples that follow.

DETAILED DESCRIPTION OF THE DISCLOSURE

As used herein, the expression "one or more" means at least one and thus includes individual components as well as mixtures/combinations.

The terms "a," "an," and "the" are understood to encompass the plural as well as the singular.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

The term "comprising" (and its grammatical variations) as used herein is used in the inclusive sense of "having" or "including" or "containing" and not in the exclusive sense of "consisting only of".

As used herein, the terms "applying a composition onto hair" and all its grammatical variations, include "contacting hair with a composition" or "exposing hair to a composition" or "layering a composition onto hair" or "treating hair with a composition" with any suitable means, for example, by using the hands or fingers, or an applicator such as a brush or comb, or by spraying, or by delivering through a nozzle or bottle cap tip.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The terms "organic acid" mean compounds containing carbon atoms and hydrogen atoms and optionally heteroatoms such as S, O, N or P, alone or in combination.

When referring to "compositions described herein," all types of compositions are intended unless specifically described otherwise. The "compositions disclosed herein" include the compositions comprising one or more reducing agent, the composition comprising one or more lactones, to oxidizing compositions, etc.

The compositions and methods of the present disclosure can comprise, consist of, or consist essentially of the essential elements and limitations of the disclosure described herein, as well as any additional or optional ingredients, components, or limitations described herein or otherwise useful.

An embodiment of the present disclosure is directed to a hair coloring composition containing, in a cosmetically acceptable solvent:
(a) one or more divalent metal salts of an inorganic acid;
(b) one or more monovalent or divalent metal salts of an organic acid; and
(c) one or more colorants chosen from oxidative dye precursors, direct dyes, pigments, and mixtures thereof.

In an embodiment, the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

In an embodiment, the one or more monovalent or divalent metal salts of an organic acid are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof.

In an embodiment, the one or more divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, their salt derivatives thereof, and mixtures thereof.

In an embodiment, the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

In an embodiment, the one or more monovalent metal salts of an organic acid includes a sodium salt and/or potassium salt.

In an embodiment, the hair coloring composition comprises one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof; and one or more divalent metal salts of an organic acid chosen from zinc lactate, zinc gluconate, zinc phenolsulfonate, zinc salicylate, zinc pyrrolidone carboxylic acid (Zinc PCA), zinc ascorbate, their derivatives thereof, and mixtures thereof.

In an embodiment, the hair coloring composition comprises one or more divalent metal salts of an inorganic acid chosen from calcium chloride and one or more divalent metal salts of an organic acid chosen from zinc gluconate.

In an embodiment, the hair coloring composition is formed from the combination of:
a color cream composition comprising one or more colorants chosen from oxidative dye precursors, direct dyes, pigments, and mixtures thereof and the cosmetically acceptable solvent; and
one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof; and
one or more monovalent or divalent metal salts of an organic acid chosen from zinc lactate, zinc gluconate, zinc phenolsulfonate, zinc salicylate, zinc pyrrolidone carboxylic acid (Zinc PCA), zinc ascorbate, their derivatives thereof, and mixtures thereof;
wherein the one or more divalent metal salts of an inorganic acid and the one or more monovalent or divalent metal salts of an organic acid are provided as separate components or together as one metal salt component.

In an embodiment, the weight ratio of the total amount of metal salts to the amount of the color cream composition is from about 5:1 to about 1:5, or from about 4:1 to about 1:4, or from about 3:1 to about 1:3, or from about 2:1 to about 1:2, or at about 1.

In an embodiment, the hair coloring composition contains in a cosmetically acceptable solvent:
(a) one or more divalent metal salts of an inorganic acid present in an amount of from about 0.5 wt. % to about 10 wt. %, based on the total weight of the hair coloring composition;
(b) one or more divalent metal salts of an organic acid present in an amount of from about 0.5 wt. % to about 10 wt. %, based on the total weight of the hair coloring composition; and
(c) one or more colorants chosen from oxidative dye precursors, direct dyes, pigments, and mixtures thereof;
wherein the hair coloring composition is capable of being mixed with an oxidizing composition in order to form a ready to use hair dye composition wherein the oxidizing composition comprises: (i) one or more oxidizing agents chosen from peroxides, urea peroxide, alkali metal bromates, ferricyanides, peroxygenated salts, perborates, percarbonates, laccases, peroxidases, redox enzymes, and mixtures thereof; and (ii) a cosmetically acceptable solvent chosen from water and a water/organic solvent mixture;
wherein the weight ratio of the total amount of metal salts to the amount of the color cream composition is from about 5:1 to about 1:5, or from about 4:1 to about 1:4, or from about 3:1 to about 1:3, or from about 2:1 to about 1:2, or at about 1.

In an embodiment, the weight ratio of the total amount of metal salts to the amount of the developer composition in the ready to use hair dye composition is from about 5:0.1 to about 1:5, or from about 4:0.1 to about 1:4, or from about 3:0.2 to about 1:3, or from about 2.8:0.2 to about 1:2.

In an embodiment, the present invention is directed to a hair coloring composition comprising, in a cosmetically acceptable solvent:
(a) one or more divalent metal salts of an inorganic acid in an amount of greater than 1 to about 20% by weight, or an amount of greater than 1 wt. % to about 6.5 wt. % or an amount of 1.1 wt. % to about 6 wt. %, or an amount of about 4 wt. % to about 6 wt. %, or an amount of about 5 wt. % to about 6 wt. %, based on the total weight of the hair coloring composition;
wherein the metal salts are chosen from metal salts of halides, metal hydroxides, metal sulfates, metal oxides, and mixtures thereof; and wherein the divalent metal is calcium, zinc, iron, nickel, copper, silver, magnesium, strontium, barium, manganese, or cobalt;
(b) one or more colorants chosen from oxidative dye precursors, direct dyes, pigments, and mixtures thereof;
wherein the composition is capable of being mixed with an oxidizing composition comprising: (i) one or more oxidizing agents; and (ii) a cosmetically acceptable solvent chosen from water and a water/organic solvent mixture;
wherein the one or more oxidizing agents are chosen from peroxides, persulfates, perborates, percarbonates, alkali metal bromates, ferricyanides, laccases, peroxidases, redox enzymes, their salts thereof, and mixtures thereof. In an embodiment, said hair coloring composition is substantially free of one or more of ammonium salt compounds, amino silicones, and cationic surfactants.

Ammonium salt compounds may be chosen from ammonium salts of halides (e.g., ammonium chloride), ammonium sals of sulfates (e.g., ammonium sulfate), and mixtures thereof.

Amino silicones may be chosen from silicones comprising at least one primary, secondary or tertiary amine or a quaternary ammonium group (i.e., a quaternized group).

Cationic surfactants may be chosen from optionally polyoxyalkylenated, primary, secondary or tertiary fatty amines, or salts thereof, and quaternary ammonium salts, and mixtures thereof.

The fatty amines generally comprise at least one C8-C30 hydrocarbon-based chain.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Use of the term "substantially free" as used herein means that the composition employs 1 wt. % or less than 1 wt. %, or less than 0.5 wt. %, or less than 0.4 wt. %, or less than 0.3 wt. %, or less than 0.2 wt. %, or less than 0.1 wt. %, or or less than 0.05 wt. % of the ingredient or material indicated.

In an embodiment, the hair coloring composition of the present disclosure comprises, in a cosmetically acceptable solvent:
(a) one or more divalent metal salts of an inorganic acid chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof;

(b) one or more monovalent or divalent metal salts of an organic acid chosen from zinc lactate, zinc gluconate, zinc phenolsulfonate, zinc salicylate, zinc pyrrolidone carboxylic acid (Zinc PCA), zinc ascorbate, sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof; and (c) one or more colorants chosen from oxidative dye precursors, direct dyes, pigments, and mixtures thereof.

In an embodiment, the weight ratio of the one or more divalent metal salts of an inorganic acid to the one or more monovalent or divalent metal salts of an organic acid is from about 10:1 to about 1:10 or from about 8:1 to about 1:8 or from about 5:1 to about 1:5 or from about 3:1 to about 1:3 or from about 2:1 to about 1:2 or at about 1, including ranges and sub-ranges therebetween.

In an embodiment, the amount of the one or more divalent metal salts of an inorganic acid is greater than the amount of the one or more monovalent or divalent metal salts of an organic acid; for example, the weight ratio of the one or more divalent metal salts of an inorganic acid to the one or more monovalent or divalent metal salts of an organic acid can be 10:1, or 9:1, or 8:1, or 7:1, or 6:1, or 5:1, or 4;1, or 3;1, or 2:1.

In an embodiment, the amount of the one or more divalent metal salts of an inorganic acid is less than the amount of the one or more monovalent or divalent metal salts of an organic acid; for example, the weight ratio of the the one or more divalent metal salts of an inorganic acid to the one or more monovalent or divalent metal salts of an organic acid can be 1:10, or 1:9, or 1:8, or 1:7, or 1:6, or 1:5, or 1:4, or 1:3, or 1:2.

It has now been surprisingly and unexpectedly discovered that the use of the compositions, methods, and kits of the present disclosure resulted in good deposit of artificial color onto hair as well as durable artificial color wherein the fading of the artificial was found to be minimal even over several shampooings of the hair.

Divalent Metal Salts of an Inorganic Acid

The one or more divalent metal salts of an inorganic acid may be chosen from metal halides, metal hydroxides, metal sulfates, metal oxides, and mixtures thereof.

The divalent metals with which the metal salts are formed are calcium, zinc, iron, nickel, copper, silver, magnesium, strontium, barium, manganese, cobalt, and mixtures thereof.

Suitable examples of the one or more divalent metal salts of an inorganic acid may be chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

In an embodiment, the one or more divalent metal salts of an inorganic acid includes a calcium salt.

In an embodiment, the calcium salt is calcium chloride.

The one or more divalent metal salts of an inorganic acid may be present in the hair coloring compositions of the present disclosure in an amount of from above 0 wt. % to about 50 wt. % or from about 0.1 wt. % to about 30 wt. % or from about 0.3 wt. % to about 20 wt. % or from about 0.4 wt. % to about 15 wt. % or from about 0.5 wt. % to about 10 wt. % or from about 0.75 wt. % to about 8 wt. %, or from about 1 wt. % to about 6.5 wt. %, including all ranges and sub-ranges therebetween, based on the total weight of the hair coloring composition.

In various embodiments, the one or more divalent metal salts of an inorganic acid is present in the hair coloring compositions of the present disclosure in a wt. % amount of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, or 6.5, based on the total weight of the hair coloring composition.

Monovalent or Divalent Metal Salts of an Organic Acid

The one or more monovalent or divalent metal salts of an organic acid may be chosen from metal salts wherein the organic acid is chosen from C1 to C9 monocarboxylic or di-carboxylic acids, polycarboxylic acids, hydroxy-carboxylic acids, and fatty acids having at least 10 carbon atoms including ascorbic acid, formic acid, acetic acid, glycolic acid, gluconic acid, lactic acid, mandelic acid, oxalic acid, maleic acid, malonic acid, glyoxylic acid, succinic acid, adipic acid, fumaric acid, sebacic acid, including citric acid, tartaric acid, malic acid, 2-hydroxy malonic acid, 2-hydroxyl n-butyl 1,2,4-tricarboxylic acid, glutaric acid, glucaric acid, 2-hydroxy n-butyl 1,3,4-tricarboxylic acid, pyrrolidone carboxylic acid, phenolsulfonic acid, and salicylic acid.

Suitable examples monovalent or divalent metal salts of an organic acid are chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof.

In an embodiment, the one or more divalent metal salts of an organic acid are chosen from zinc lactate, zinc gluconate, zinc phenolsulfonate, zinc salicylate, zinc pyrrolidone carboxylic acid (Zinc PCA), zinc ascorbate, zinc citrate, their salt derivatives thereof, and mixtures thereof.

In an embodiment, the one or more divalent metal salts of an organic acid includes a zinc salt.

In an embodiment, the zinc salt is zinc gluconate.

In an embodiment, the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

In an embodiment, the one or more monovalent metal salts of an organic acid includes a sodium salt and/or potassium salt.

The one or more monovalent or divalent metal salts of an organic acid may be present in the hair coloring compositions of the present disclosure in an amount of from above 0 wt. % to about 50 wt. % or from about 0.1 wt. % to about 30 wt. % or from about 0.3 wt. % to about 20 wt. % or from about 0.4 wt. % to about 15 wt. % or from about 0.5 wt. % to about 10 wt. % or from about 0.75 wt. % to about 8 wt. %, or from about 1 wt. % to about 6.5 wt. %, including all ranges and sub-ranges therebetween, based on the total weight of the hair coloring composition.

In various embodiments, the one or more monovalent or divalent metal salts of an organic acid is present in the hair coloring compositions of the present disclosure in a wt. % amount of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, or 6.5, based on the total weight of the hair coloring composition.

Cosmetically Acceptable Solvent (or Carrier)

The compositions of the present disclosure may be presented in a cosmetically acceptable solvent. This cosmetically acceptable solvent may include, for example, water or a mixture of water and at least one cosmetically acceptable organic solvent.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin.

The organic solvents for use in the present disclosure can be volatile or non-volatile compounds.

The cosmetically acceptable solvent may be employed according to the present disclosure in an amount ranging from about 5% to about 95% by weight, or such as from about 20% to about 90% by weight, such as from about 30 to about 80% by weight, or such as from about 35% to about 75% by weight, such as from about 5 to about 50% by weight, such as from about 50 to 95% by weight, based on the total weight of the composition.

The organic solvent may be employed according to the present disclosure in an amount ranging from about 0.1% to about 25% by weight, such as from about 1% to about 15% by weight, or such as from about 3% to about 10% by weight, or such as from about 5% to about 10% by weight, based on the total weight of the composition of the present disclosure.

Colorants

The coloring compositions of the present disclosure include at least one colorant compound chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta.-hydroxyethyloxy-para-phenylenediamine, 2-.beta.-acetylaminoethyloxy-para-phenylenediamine, N-(.beta.-methoxyethyl)-para-phenylenediamine, 4-aminophenylpyrrolidine, 2-thienyl-para-phenylenediamine, 2-.beta.-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(.beta.-hydroxyethyl)-para-phenylenediamine, 2-chloro-para-phenylenediamine and 2-.beta.-acetylaminoethyloxy-para-phenylenediamine, and the addition salts thereof with an acid, are particularly preferred.

Among the bis(phenyl)alkylenediamines that may be mentioned, for example, are N,N'-bis(.beta.-hydroxyethyl)-N,N'-bis(4'-aminophenyl)-1,3-diaminopropano-I, N,N'-bis(.beta.-hydroxyethyl)-N,N'-bis(4'-aminophenyl)ethylenediamine, N,N'-bis(4-aminophenyl)tetramethylenediamine, N,N'-bis(.beta.-hydroxyethyl)-N,N'-bis(4-aminophenyl)tetramethylenediamin-e, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:
(a) one (di)($C_1$-$C_6$)(alkyl)amino group wherein said alkyl group can be substituted by at least one hydroxy, amino, imidazolium group;
(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or
(c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-o-ne. 2,3-Diamino-6,7-dihydro-1H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition according to the present disclosure may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(.beta.-hydroxyethyl)amino-2-methyl-phenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(.beta.-hydroxyethyloxy)benzene, 2-amino-4-(.beta.-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-.beta.-hydroxyethylamino-3,4-methylene-dioxybenzene, .alpha.-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(.beta.-hydroxyethyl)amino-3,4-methylene-dioxybenzene, 2,6-bis(J-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present disclosure.

The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VII) below:

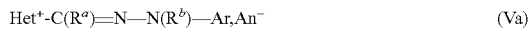  (Va)

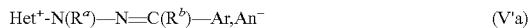  (V'a)

  (VIa)

  (VI'a) and

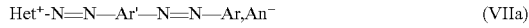  (VIIa)

in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar$^+$ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, represent a hydrogen atom or a group ($C_1$-$C_8$)alkyl, which is optionally substituted, preferentially with a hydroxyl group;

or alternatively the substituent $R^a$ with a substituent of Het$^+$ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group ($C_1$-$C_4$)alkyl, which is optionally substituted with a hydroxyl group;

An$^-$ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

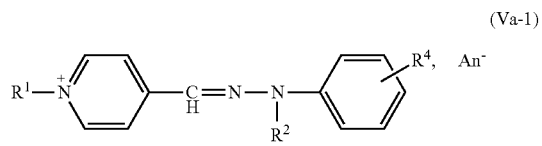

(Va-1)

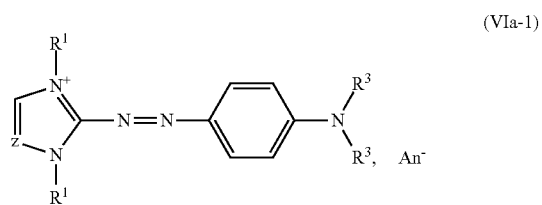

(VIa-1)

formulae (V-1) and (VI-1) with:

$R^1$ representing a ($C_1$-$C_4$) alkyl group such as methyl;

$R^2$ and $R^3$, which are identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group(s) with a hydroxyl group; particularly, $R^4$ is a hydrogen atom, Z represents a CH group or a nitrogen atom, preferentially CH;

An$^-$ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

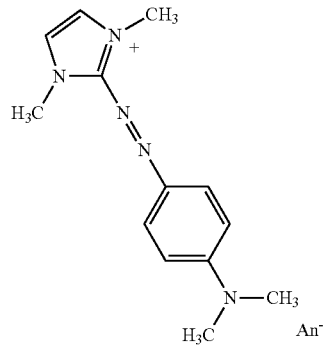

Basic Red 51

-continued

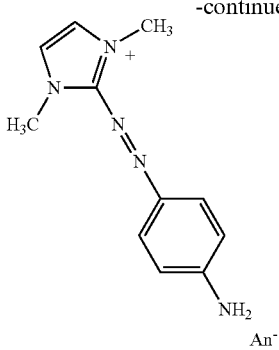

Basic Orange 31

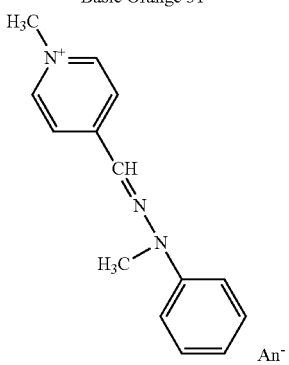

Basic Yellow 87

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present disclosure.

Alkalizing Agents

The hair coloring composition may have a pH that is alkaline. Exemplary pH's include 7, 8, 9, 10, 11, 12, 13 or 14. In some embodiments, the pH of the hair coloring composition may range from about 7, 8, or 9 to about 9, 10, 11 or 12.

The alkalinity of the hair coloring composition may be derived from one or more alkalizing agents. In some embodiments, the alkalizing agent may ammonia or an ammonia gas-generating compound and/or an amine or ammonium-based compound in amounts sufficient to make such compositions alkaline. In further embodiments, the alkalizing agent may be selected from alkanolamines, such as monoethanolamine (MEA) and isopropanolamine. Alkalinity may be derived from ammonium compounds as well (e.g., NH4OH).

The one or more alkalizing agents may be present in amounts ranging from greater than about 0, or from 1, 2, 3, 4, 5, 10 to about 5, 10, 13, 15, 18, 20, 25 or 30% by weight of the total composition.

Oxidizing Agents

Oxidizing agents may be selected from, for example, peroxides, persulfates, perborates percarbonates, alkali metal bromates, ferricyanides, peroxygenated salts, or mixtures thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the oxidizing agent is hydrogen peroxide present in an aqueous solution whose titre may range from 1 to 40 volumes, such as from 5 to 40 volumes or such as from 5 to 20 volumes.

In other cases, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof. Hydrogen peroxide may commonly be used as the oxidizing agent.

In an embodiment, the oxidizing agent is hydrogen peroxide and is provided as an oxidizing (developer) composition.

In general, the oxidizing agent will be present in an amount of from about 0.05 to about 50% by weight, such as from about 0.1% to about 30% by weight, or such as from about 0.1% to about 20% by weight, or such as from about 1% to about 10% by weight, based on the total weight of the oxidizing composition.

In some instances, the oxidizing composition is aqueous or is in the form of an emulsion.

In other instances, the oxidizing composition is substantially anhydrous. The term "substantially anhydrous" means that the oxidizing composition is either completely free of water or contains no appreciable amount of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, chosen from water, organic solvents, and mixtures thereof. When the oxidizing composition is substantially anhydrous, the oxidizing composition may comprise at least one solvent chosen from organic solvents. Suitable organic solvents for use in the oxidizing composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The organic solvent may, for example, be present in an amount ranging from about 0.5% to about 70% by weight, such as from about 2% to about 60% by weight, preferably from about 5 to about 50% by weight, relative to the total weight of the oxidizing composition.

The oxidizing composition may be in the form of a powder, gel, liquid, foam, lotion, cream, mousse, and emulsion.

The oxidizing composition of the present disclosure my also contain at least one fatty substance as described above. Thus, the total amount of fatty substances in the combination or mixture of the coloring and oxidizing compositions of the present disclosure may range from about 10% to about 80% by weight, or such as from about 20% to about 60% by weight, or such as from about 20% to about 40% by weight, or such as from about 20% to about 30% by weight, based on the total weight of the composition.

Auxiliary Agents

Auxiliary ingredients may be added to the coloring and/or oxidizing (developer) composition of the present disclosure. Exemplary auxiliary ingredients useful according to various embodiments of the disclosure include, but are not limited to, rheology-modifying agents, surfactants (cationic, anionic, non-ionic and/or amphoteric/zwitterionic surfactants), bleach activators and co-bleach activators, chelants, fatty substances, ceramides, alkoxyaminosilicones, silanes, and lift-enhancing agents, such as nitrogen-containing compounds and metal catalyst compounds, and preservatives.

The coloring and/or oxidizing (developer) composition may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The compositions may contain one or more rheology or viscosity modifying agents, such as viscosity increasing agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

Forms

The compositions described herein may be in any suitable physical form. Suitable forms include, but are not limited to low to moderate viscosity liquids, creams, lotions, milks, mousses, sprays, gels, and the like. Suitable excipients, such as those listed above, are included or excluded from the hair coloring formulation depending on the form of use of the formulation (e.g., spray, cream, gel, etc.).

i. Creams

The compositions disclosed herein for coloring hair may be in the form of a cream. The cream can be prepared as emulsions, for example, oil in water or water in oil or water in oil in water emulsions and will generally contain one or more of emulsifying agents, nonionic surfactants, anionic surfactants, cationic agents, conditioning agents, fatty alcohols, oils, and mixtures thereof.

ii. Gels

The compositions disclosed herein for coloring hair may be in the form of a gel. The gels will typically contain a cosmetically acceptable carrier such as water and will generally contain one or more of gelling agents, structuring agents, rheology or viscosity modifying agents, and mixtures thereof.

iii. Spray

The compositions described herein for coloring hair may be in the form of a spray. The spray typically includes the coloring composition in a cosmetically acceptable carrier. In some embodiments, the carrier is water or a water and alcohol mixture. The spray formulation optionally includes an emollient, thickener, hair conditioning agent, polymer, and/or surfactant. The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair color formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

Compositions, Kits, and Methods

The invention of the present disclosure pertains to a hair coloring composition comprising, in a cosmetically acceptable solvent:
  (a) one or more divalent metal salts of an inorganic acid;
  (b) one or more monovalent or divalent metal salts of an organic acid; and
  (c) one or more colorants chosen from oxidative dye precursors, direct dyes, pigments, and mixtures thereof.

The invention of the present disclosure also pertains to a hair coloring composition comprising, in a cosmetically acceptable solvent:
  (a) one or more divalent metal salts of an inorganic acid in an amount of greater than 1 to about 20% by weight, based on the total weight of the hair coloring composition;
  wherein the metal salts are chosen from metal salts of halides, metal hydroxides, metal sulfates, metal oxides, and mixtures thereof; and wherein the divalent metal is calcium, zinc, iron, nickel, copper, silver, magnesium, strontium, barium, manganese, or cobalt; and
  (b) one or more colorants chosen from oxidative dye precursors, direct dyes, pigments, and mixtures thereof.

Any of the above hair coloring composition may further comprise a developer containing an oxidizing agent (e.g., hydrogen peroxide) and/or alkalizing agent in order to form a ready to use hair dye composition. In some embodiments, the developer may be in a separate container from the hair coloring composition.

In an embodiment of the present disclosure, a monovalent or divalent metal salt of an organic acid (e.g. zinc-based compound) and/or a divalent metal salt of an organic acid (e.g. an alkaline earth metal salt such as a calcium chloride) are first added as separate components or as one metal salt component into a color cream composition containing the one or more colorants chosen from oxidative dye precursors, direct dyes, pigments, and mixtures thereof in order to form the hair coloring composition. The developer is then combined with the hair coloring composition.

In an embodiment of the present disclosure, a dye mixture is first formed from the combination of a color cream composition containing the one or more colorants chosen from oxidative dye precursors, direct dyes, pigments, and mixtures thereof and the developer. The monovalent or divalent metal salt of an organic acid (e.g. zinc-based compound) and/or a divalent metal salt of an inorganic acid (e.g. an alkaline earth metal salt such as a calcium chloride) are then added as separate components or as one metal salt component into the dye mixture to form a ready to use hair dye composition.

In an embodiment of the present disclosure, the weight ratio of the total amount of metal salts to the amount of the color cream composition is from about 5:1 to about 1:5, or from about 4:1 to about 1:4, or from about 3:1 to about 1:3, or from about 2:1 to about 1:2, or at about 1, including ranges and sub-ranges therebetween.

In an embodiment of the present disclosure, the weight ratio of the total amount of metal salts to the amount of the developer composition in the ready to use hair dye composition is from about 5:0.1 to about 1:5, or from about 4:0.1 to about 1:4, or from about 3:0.2 to about 1:3, or from about 2.8:0.2 to about 1:2, including ranges and sub-ranges therebetween.

Another aspect of the invention pertains to kits comprising the coloring and developer compositions described herein. For example, developer may be present in a separate container from the coloring composition which comprises the above-described metal salts and colorants. The coloring composition may, in some embodiments, be ready for mixing with the developer. In such embodiments, the developer and hair coloring composition are combined just prior to use.

In other embodiments, each of the above-described components of the hair coloring composition (metal salts and colorants) are packaged in separate containers. In an embodiment, the one or more divalent metal salts of an inorganic acid (a), the one or more monovalent or divalent metal salts of an organic acid (b) and the one or more colorants chosen from oxidative dye precursors, direct dyes, pigments, and mixtures thereof (c) can be packaged in three separate containers. In another embodiment, the metal salts (a) and (b) can be packaged together in one container and the colorants can be packaged in another container. In yet another embodiment, one of the metal salts (a) or (b) can be packaged with the colorants (c) in one container and the remaining metal salt component is packaged in another container. The contents of the containers in these various embodiments can then be mixed in any order to form the hair coloring composition.

In an embodiment, when the one or more metal salt components (a) or (b) are packaged separately from the colorants, the metal salt component can be mixed with the developer composition. The resulting metal salt-developer composition can then be combined with the colorants (which can be in an aqueous or emulsion or cream or gel form) in order to form a ready to use dye composition for coloring the hair.

When the one or more of the metal salt components (a) or (b) are packaged separately from the colorants, the metal salt component can be in anhydrous or substantially form (for example, powder or wet powder form) or in liquid form (for example, aqueous form in water or emulsion/lotion form or serum).

Another aspect of the invention pertains to methods of using the coloring compositions and dye compositions resulting from the combination of the coloring composition and oxidizing composition (developer). The methods comprise applying the dyes compositions described herein to human hair. The dye composition may be left on the hair for a period of time sufficient to achieve the desired alteration in hair tone. For example, the dye composition may be left on the hair for up to one hour, such as from about 3 minutes to about 45 minutes, from about 5 minutes to about 30 minutes, or from about 10 minutes to about 20 minutes. In further embodiments, the dye composition may be left on the hair for a period up to about 30 minutes, such as, for example, from about 1 to about 30 minutes, about 1 to about 10 minutes, or about 1 to about 5 minutes. One skilled in the art will, by considering various factors such as the starting and desired tones of the hair, be able to determine an appropriate amount of time to leave the dye composition on the hair in order to achieve the desired alteration in hair tone. By way of non-limiting example, various embodiments according to the disclosure may provide for an increase of 1 to 4 in the tone height of the hair.

In some embodiments, the dye composition may, optionally, be shampooed and/or rinsed off the hair.

Thus, another aspect of the invention pertains to a method for artificially coloring hair and/or inhibiting the artificial coloring from fading, the method comprising contacting hair with a ready to use dye composition for a sufficient period of time to achieve a desired color of the hair and/or alteration of the color of hair; wherein the ready to use dye composition is formed from the combination of any one of the hair coloring compositions of the present disclosure with an oxidizing composition containing: (i) one or more oxidizing agents chosen from peroxides, urea peroxide, alkali metal bromates, ferricyanides, peroxygenated salts, perborates, percarbonates, laccases, peroxidases, redox enzymes, and mixtures thereof, and (ii) a cosmetically acceptable solvent selected from water and a water/organic solvent mixture.

Implementation of the present disclosure is provided by way of the following examples. The examples serve to illustrate the technology without being limiting in nature.

EXAMPLES

General Procedures

Normal bleached hair swatches (from International Hair Importers, HIP) were treated and evaluated as set forth below.

Color Treatment: The hair swatches were colored/dyed with a dye mixture containing color cream composition and a developer composition for a period of time to give a desired color to the hair. The color cream composition contained oxidative dyes and the developer contained an oxidizing agent (hydrogen peroxide). The developer composition can employ different amounts of the oxidizing agent depending on the desired lift or lightening of the color on the hair. For example, a 20 volume developer means that it contains 6 wt. % of an oxidizing agent; a 10 volume developer means that it contains 3 wt. % of an oxidizing agent; a 3 volume developer means that it contains 0.9 wt. % of an oxidizing agent.

The weight ratio of the color cream composition to the developer in the present disclosure can range from about 1:4 to about 5:0.2, or from about 1:3 to about 4.8:0.2, or from about 1:2 to about 4.8:0.2, or from about 1.5:2 to about 4.8:0.2, or from about 1.5:2.25 to about 4.8:0.2, or from about 1:1 to about 4.8:0.2.

In various embodiments, weight ratio of the color cream composition to the developer in the present disclosure is at about 2:3, or about 3:3, or about 1:2, or about 2:2, or about 1:1, or about 1.5:2, or about 1.5:2.25, or about 1:1.5, or about 1.5:2.5, or about 4:1, or about 3:0.5, or about 4.8:0.2.

In various examples and in accordance with the present disclosure, a divalent metal salt of an inorganic acid (e.g., calcium chloride) and/or divalent metal salt of an organic acid (e.g., zinc gluconate), were added to the color cream composition before the color cream composition was mixed with a developer. For a control treatment, the color cream composition did not contain either of the divalent metal salt of an organic acid and/or the divalent metal salt of an inorganic acid; instead, water in an amount equivalent to that of the total amount of metal salt used was added to the color cream composition.

In other examples and in accordance with the present disclosure, a divalent metal salt of an inorganic acid (e.g., calcium chloride) and/or divalent metal salt of an organic acid (e.g., zinc gluconate), were added to the dye mixture formed from the combination of the color cream composition with a developer. For a control treatment, the dye mixture did not contain either of the divalent metal salt of an organic acid and/or the divalent metal salt of an inorganic acid; instead, water in an amount equivalent to that of the total amount of metal salt used was added to the dye mixture.

Hair Color Protection Evaluation:

The treated hair swatches were washed with a shampoo (sodium laureth sulfate shampoo), then rinsed with water (a shampoo cycle). The hair swatches were then blow dried. For evaluations of hair color protection or wash-resistant hair color, the color of the dyed hair was assessed after one or more shampoo cycles (can range from one up to twenty shampoo cycles).

Hair Color Deposit Evaluation:

The treated hair swatches were rinsed with water and dried. The color of the dyed hair was then assessed.

Color Assessment:

For determining the degree of change in the color of hair and/or the degree of lightening of the color or degree of color deposit on hair, colorimetric measurements of L*, a*, and b* values of the hair swatches were obtained. The L*a*b* colorimetric system is a colorimetric system that assigns each color to a position in a spherical color space. In this color space, the brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive direction of the y-axis corresponds to a yellow direction, the negative direction of the x-axis corresponds to a green direction, the negative direction of the y-axis corresponds to a blue direction, and the position on the x-axis is designated by a* of which value changes from −60 to +60 and the position on the y-axis is designated by b* of which value changes from −60 to +60. The hue and chroma are represented by a* value and b* value, respectively.

Thus, the greater the value of L*, the lighter or less intense is the color of the hair. Conversely, the lower the value of L*, the darker or more intense is the color of the hair (this can also indicate greater color deposit when the hair is colored or dyed). The a* value (green/red color axis) and b* value (blue/yellow color axis) represent hue and chroma, respectively. The higher the a*, the more the hue shifts to red (i.e., the hair is redder); and the lower the b*, the more the chroma value shifts to blue. Delta-E (ΔE) which is calculated from the L*, a*, and b* values represents the overall color change on the swatches (from control or baseline). Generally, if ΔE is less than 1.0 there is hardly any color difference that the human eye can see. If ΔE is greater than 1.0, then there is a noticeable color difference.

Example 1 (Color Deposit)

Normal bleached hair was dyed to a red color with dye mixtures comprising a color cream composition and a developer (20 volume or 10 volume; hydrogen peroxide) in the weight ratios per gram of hair as follows:

TABLE 1

| Dye Mixture | Amount (g) of color cream composition | Amount (g) of divalent metal salt of inorganic acid (10 wt. % of calcium chloride in water) added to color cream composition | Amount (g) of divalent metal salt of organic acid (10 wt. % of zinc gluconate in water) added to color cream composition | Amount (g) of water added to color cream composition | Amount (g) of developer composition |
|---|---|---|---|---|---|
| Dye A or Dye D | 2 | 0.5 | 0 | 0.5 | 3 |
| Dye B or Dye E | 2 | 0 | 0.5 | 0.5 | 3 |
| Dye C or Dye F | 2 | 0.5 | 0.5 | 0 | 3 |

For the control treatment, water in an amount equivalent to that of the total weight of metal salt solutions added was included in the color cream composition.

The various test dye mixtures are described in Tables 2 and 3 below. The measured L* and ΔE values of the colored hair are also reported in the tables.

TABLE 2

| Dye Mixture (20 vol developer) (30 minute processing time on hair) | % by weight of metal salt in total weight of the color cream composition** | | L* Value | Delta-E (ΔE) |
|---|---|---|---|---|
| | Divalent metal salt of inorganic acid (Calcium Chloride) | Divalent metal salt of organic acid (Zinc Gluconate) | | |
| Control Dye* | 0 | 0 | 26.1 | — |
| Dye A | 1.67 | 0 | 26.2 | 1.16 |
| Dye B | 0 | 1.67 | 26.3 | 1.56 |
| Dye C (invention) | 1.67 | 1.67 | 25.7 | 2.75 |

*Control dye mixture did not contain any of the metal salts.
**when mixed with the developer, each resulting dye A, B, or C contained 0.83 wt. % of each of calcium chloride and/or zinc gluconate

TABLE 3

| Dye Mixture (10 vol developer) (20 minute processing time) | % by weight of metal salt in total weight of the color cream composition** | | L* Value | Delta-E (ΔE) |
|---|---|---|---|---|
| | Divalent metal salt of inorganic acid (Calcium Chloride) | Divalent metal salt of organic acid (Zinc Gluconate) | | |
| Control Dye* | 0 | 0 | 26.7 | — |
| Dye D | 1.67 | 0 | 26.2 | 1.27 |
| Dye E | 0 | 1.67 | 25.2 | 2.11 |
| Dye F (invention) | 1.67 | 1.67 | 24.6 | 4.99 |

*Control dye mixture did not contain any of the metal salts.
**when mixed with the developer, each resulting dye A, B, or C contained 0.83 wt. % of each of calcium chloride and/or zinc gluconate The results in tables 2 and 3 show that unexpectedly: (i) the amount of color deposit and degree of color change with the dye mixtures containing calcium chloride (CaCl2)) and zinc gluconate were greater than the amount of color deposit and color change provided by CaCl2) or zinc gluconate alone, and (ii) the color deposit and degree of color change with the dye mixtures containing CaCl2) and zinc gluconate was even greater at lower amounts of oxidizing agent (10 volume developer) at shorter processing time, These results are evident from the lower L* values and higher delta-E values obtained with the dye containing CaCl2) and zinc gluconate (Dye C or F) as compared to the L* values obtained with the control dyes or with the dyes containing CaCl2) alone or zinc gluconate alone (lower L* values denote darker color or more color deposit and the higher delta-E values denote greater color changes as calculated from the controls).

The colorimetric results also correspond to the visual observations wherein the differences in color deposition and delta-E can be perceived by the eye.

Example 2 (Color Deposit)

Normal bleached hair was dyed to a natural brown color with dye mixtures comprising a color cream composition and a developer (20 volume or 3 volume; hydrogen peroxide) in the following weight proportions per gram of hair:

TABLE 4

| Dye Mixture | Amount (g) of color cream composition | Amount (g) of divalent metal salt of inorganic acid (10 wt. % of calcium chloride in water) added to color cream composition | Amount (g) of divalent metal salt of organic acid (10 wt. % of zinc gluconate in water) added to color cream composition | Amount (g) of water added to color cream composition | Amount (g) of developer composition |
|---|---|---|---|---|---|
| Dye G or Dye J | 1 | 0.5 | 0 | 0.5 | 2 |
| Dye H or Dye K | 1 | 0 | 0.5 | 0.5 | 2 |
| Dye I or Dye L | 1 | 0.5 | 0.5 | 0 | 2 |

For the control treatment, water in an amount equivalent to that of the total weight of metal salt solutions added was included in the color cream composition.

The various test dye mixtures are described in Tables 5 and 6 below. The measured L* and ΔE values of the colored hair are also reported in the tables.

TABLE 5

| Dye Mixture (20 vol developer) (30 minute processing time) | % by weight of metal salt in total weight of the color cream composition** | | L* Value | Delta-E (ΔE) |
|---|---|---|---|---|
| | Divalent metal salt of inorganic acid (Calcium Chloride) | Divalent metal salt of organic acid (Zinc Gluconate) | | |
| Control Dye* | 0 | 0 | 31.8 | — |
| Dye G | 1.67 | 0 | 29.9 | 2.58 |
| Dye H | 0 | 1.67 | 30.3 | 2.19 |
| Dye I (invention) | 1.67 | 1.67 | 28.8 | 4.50 |

*Control dye mixture did not contain any of the metal salts.
**when mixed with the developer, each resulting dye G, H, or I contained 1.25 wt. % of each of calcium chloride and/or zinc gluconate.

TABLE 6

| Dye Mixture (3 vol developer) (30 minute processing time) | % by weight of metal salt in total weight of the color cream composition** | | L* Value | Delta-E (ΔE) |
|---|---|---|---|---|
| | Divalent metal salt of inorganic acid (Calcium Chloride) | Divalent metal salt of organic acid (Zinc Gluconate) | | |
| Control Dye* | 0 | 0 | 39.9 | — |
| Dye J | 1.67 | 0 | 33.3 | 8.05 |
| Dye K | 0 | 1.67 | 33.9 | 6.99 |
| Dye L (invention) | 1.67 | 1.67 | 31.7 | 10.10 |

*Control dye mixture did not contain any of the metal salts.
**when mixed with the developer, each resulting dye J, K, or L contained 1.25 wt. % of each of calcium chloride and/or zinc gluconate.

The results in tables 5 and 6 show that unexpectedly: (i) the amount of color deposit and degree of color change with the dye mixtures containing CaCl2) and zinc gluconate were greater than the amount of color deposit provided by CaCl2) or zinc gluconate alone (comparatives), and (ii) the color deposit and degree of color change with the dye mixtures containing CaCl2) and zinc gluconate was comparable or even higher at lower amounts of oxidizing agent (3 volume developer) at the same amount of processing time compared to the color deposit at much higher amounts of oxidizing agent (20 volume developer), These results are evident from the lower L* values and higher delta-E values obtained with the dye containing CaCl2 and zinc gluconate (Dye I or L) as compared to the L* values obtained with the control dyes or with the dyes containing CaCl2 alone or zinc gluconate alone (lower L* values denote darker color or more color deposit and the higher delta-E values denote greater color changes as calculated from the controls).

The colorimetric results also correspond to the visual observations wherein the differences in color deposition and delta-E can be perceived by the eye.

Example 3

(Color Deposit and Varying the Amounts of Salt and Oxidizing Agent)

One gram normal bleached hair swatches were dyed to an auburn color with dye mixtures formed from combining a color cream composition (with and without calcium chloride) and a developer (20 volume; hydrogen peroxide) according to table 5:

TABLE 7

| Dye Mixture | Amount (g) of color cream composition | Amount (g) of divalent metal salt of inorganic acid (10 wt. % of calcium chloride in water) added to the color cream composition | Amount (g) of water added to the color cream composition | Amount (g) of developer composition |
|---|---|---|---|---|
| Dye M | 2 | 2.8 | 0 | 0.2 |
| Dye N | 2 | 2 | 0 | 1 |

For the control dye mixtures for Dyes M and N, water in an amount equivalent to that of the total weight of metal salt solution added was included in the color cream composition.

The measured $L^*$ values of the colored hair are also reported in Table 6.

TABLE 8

| Dye Mixture (20 vol developer) (30 min processing time) | % by weight of $CaCl_2$ in total weight of the color cream composition | by weight of % $CaCl_2$ in total weight of the dye mixture | $L^*$ Value |
|---|---|---|---|
| Control Dye* | 0 | 0 | 29.4 |
| Dye M | 5.83 | 5.6 | 21.5 |
| Control Dye* | 0 | 0 | 24.8 |
| Dye N | 5 | 4 | 22.8 |

*Control dye mixture did not contain an alkaline earth metal salt.

The results in table 8 show that the addition of calcium chloride in the color cream composition resulted in greater color deposit of the dye onto the hair as compared to the controls as evident from the lower $L^*$ values which denote darker color or more color deposit.

The results also show that as the amount of calcium chloride slightly increased from 5 wt. % to 5.83 wt. %, the degree of color deposit also significantly increased (greater decrease in $L^*$ value from the control), even when the amount of developer (i.e., oxidizing agent) decreased from 1 g to 0.2 g. These results indicate that even at lower amounts of oxidizing agent in the dye mixture, more color can be deposited with a small increase in the amount of calcium chloride. Less amount of oxidizing agent in a dye composition is desirable since this reduces or minimizes the damage to the hair which is partly caused by oxidizing agents in dyes.

The colorimetric results also correspond to the visual observations wherein the differences in color deposition and delta-E can be perceived by the eye.

Example 4 (Hair Color Protection)

Protocol:

One gram hair swatches 1 and 3 were colored with the following dye mixtures formed from mixing a color cream composition and a developer composition (hydrogen peroxide) in the indicated weight ratios: 1.5 g of color cream composition: 2.25 g of 20 Volume developer.

One gram swatches 2 and 4 were colored with the following dye mixtures containing calcium chloride and zinc gluconate salts (in powder form) as prepared in the following weight ratios: 1.5 g of Color Cream: 2.25 g of 20 Volume developer: 0.0375 g of calcium chloride and 0.0375 g of zinc gluconate added to the color cream resulting in 2.4 wt. % of each salt based on the weight of the color cream composition or 1 wt. % of each salt based on the weight of the dye mixture (color cream+developer).

The color processing time for all swatches was 30 minutes after which the swatches were rinsed and dried to remove excess dye. $L^*a^*b^*$ colorimetric measurements were taken after the initial coloration. The swatches were then subjected to 10 shampoo cycles according to the general procedure above. $L^*a^*b^*$ colorimetric measurements were then taken after the 10th and final shampoo cycle in order to assess the color evolution of the swatches over the 10 shampoo cycles. The change in the total color ($\Delta E$) for each swatch was then calculated based on the changes in $L^*a^*b^*$ values (from the initial color to the color after the 10th shampoo cycle).

TABLE 6

| Swatch | In-Color Treatment (dye mixture) % by weight of metal salt in total weight of the dye mixture | $L^*$ after initial coloration | $\Delta E$ relative to control after initial coloration | $\Delta E$ relative to control after 10 shampoo cycles |
|---|---|---|---|---|
| 1-control | 0 wt % metal salt | 27.29 | — | — |
| 2 | 1 wt. % $CaCl_2$ 1 wt. % ZnGlu | 24.76 | 4.71 | 4.92 |
| 3-control | 0 wt. % metal salt | 24.02 | — | — |
| 4 | 1 wt. % $CaCl_2$ 1 wt. % ZnGlu | 20.93 | 6.08 | 7.42 |

SUMMARY

The data in the table above indicate that the addition of both Calcium Chloride ($CaCl2$)) and Zinc Gluconate ("Zn-Glu") into the dye mixture unexpectedly enhanced the initial deposition of color on hair as demonstrated by lower $L^*$ values (color is darker).

In addition, the $\Delta E$ values of >4 after initial coloration for the swatches treated with the dye mixture containing $CaCl2$) and ZnGlu correspond to a color change or deposit in that is easily detected by or visible to the naked eye when compared to the swatches treated with dye mixtures that did not contain $CaCl2$) and ZnGlu.

Surprisingly and unexpectedly, after 10 shampoos, the $\Delta E$ values for the swatches treated with the dye mixture containing $CaCl2$) and ZnGlu did not change significantly as compared to the $\Delta E$ values after initial coloration. This shows that the color on the hair was resistant to fading or shampoo-resistant even after 10 shampoo/wash cycles.

The colorimetric results also correspond to the visual observations wherein the differences in color deposition and delta-E can be perceived by the eye.

From the results in the examples above, it is evident that the hair treated according to the inventive method and compositions exhibited significant improvements in both color deposit and color change. It is also evident that the durability of the color in the hair that was treated according to the inventive method and compositions was improved over multiple washings/shampooings (up to as much as 10 shampoos).

All values set forth herein can be modified with the term "about," if desired to impart the meaning above, or recited without the term in order to have their ordinary meaning, regardless of whether the term "about" is specifically set forth (or is absent) in conjunction with any particular value in the specification.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair coloring composition comprising, in a cosmetically acceptable solvent:
   (a) above 0 wt. % to about 50 wt. % of one or more divalent metal salts of an inorganic acid chosen from salts of calcium, zinc, iron, nickel, copper, silver, magnesium, strontium, barium, manganese, cobalt, and mixtures thereof;
   (b) above 0 wt. % to about 50 wt. % of one or more monovalent or divalent metal salts of an organic acid, wherein
      the one or more divalent metal salts of an organic acid are chosen from salts of calcium, zinc, iron, nickel, copper, silver, magnesium, strontium, barium, manganese, cobalt, and mixtures thereof,
      the one or more monovalent metal salts of an organic acid are chosen from salts of lithium, sodium, potassium, copper, silver, and mixtures thereof, and
      the organic acid of the one or more monovalent or divalent metal salts of an organic acid is chosen from C1 to C9 monocarboxylic or di-carboxylic acids, polycarboxylic acids, hydroxy-carboxylic acids, and fatty acids having at least 10 carbon atoms; and
   (c) one or more colorants chosen from oxidative dye precursors, direct dyes, pigments, and mixtures thereof.

2. The hair coloring composition of claim 1, wherein the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

3. The hair coloring composition of claim 1, wherein the one or more divalent metal salts of an inorganic acid includes a calcium salt.

4. The hair coloring composition of claim 3, wherein the calcium salt is calcium chloride.

5. The hair coloring composition of claim 1, wherein the one or more divalent metal salts of an inorganic acid are present in an amount of from about 0.75 wt. % to about 8 wt. %, based on the total weight of the hair coloring composition.

6. The hair coloring composition of claim 1, wherein the one or more divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, their salt derivatives thereof, and mixtures thereof.

7. The hair coloring composition of claim 1, wherein the one or more divalent metal salts of an organic acid includes a zinc salt.

8. The hair coloring composition of claim 7, wherein the zinc salt is zinc gluconate.

9. The hair coloring composition of claim 1, wherein the one or more monovalent metal salts of an organic acid are chosen from sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, and mixtures thereof.

10. The hair coloring composition of claim 1, wherein the one or more monovalent or divalent metal salts of an organic acid are present in an amount of from about 0.75 wt. % to about 8 wt. %, based on the total weight of the hair coloring composition.

11. The hair coloring composition of claim 1, wherein the composition comprises one or more divalent metal salts of an inorganic acid chosen from calcium chloride and one or more divalent metal salts of an organic acid chosen from zinc gluconate.

12. The hair coloring composition of claim 1, wherein the hair coloring composition is formed from the combination of:
   a color cream composition comprising the one or more colorants chosen from oxidative dye precursors, direct dyes, pigments, and mixtures thereof and the cosmetically acceptable solvent; and
   the one or more divalent metal salts of an inorganic acid; and
   the one or more monovalent or divalent metal salts of an organic acid;
      wherein the one or more divalent metal salts of an inorganic acid and the one or more monovalent or divalent metal salts of an organic acid are provided as separate components or together as one metal salt component.

13. The hair coloring composition of claim 12, wherein the weight ratio of the total amount of metal salts to the amount of the color cream composition is from about 5:1 to about 1:5.

14. The hair coloring composition of claim 1, further comprising one or more oxidizing agents or capable of being mixed with an oxidizing composition comprising: (i) one or more oxidizing agents; and (ii) a cosmetically acceptable solvent chosen from water and a water/organic solvent mixture; wherein the one or more oxidizing agents are chosen from peroxides, persulfates, perborates, percarbonates, alkali metal bromates, ferricyanides, laccases, peroxidases, redox enzymes, their salts thereof, and mixtures thereof.

15. A hair coloring composition comprising, in a cosmetically acceptable solvent:
   (a) one or more divalent metal salts of an inorganic acid present in an amount of from about 0.5 wt. % to about 10 wt. %, based on the total weight of the hair coloring composition and chosen from calcium chloride, calcium sulfate, calcium nitrate, calcium carbonate and hydrogen carbonate, calcium phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof;
- (b) one or more divalent metal salts of an organic acid present in an amount of from about 0.5 wt. % to about 10 wt. %, based on the total weight of the hair coloring composition and chosen from zinc lactate, zinc gluconate, zinc phenolsulfonate, zinc salicylate, zinc pyrrolidone carboxylic acid (Zinc PCA), zinc ascorbate, and mixtures thereof; and
- (c) one or more colorants chosen from oxidative dye precursors, direct dyes, pigments, and mixtures thereof; wherein the hair coloring composition is capable of being mixed with an oxidizing composition comprising: (i) one or more oxidizing agents chosen from peroxides, urea peroxide, alkali metal bromates, ferricyanides, peroxygenated salts, perborates, percarbonates, laccases, peroxidases, redox enzymes, and mixtures thereof; and (ii) a cosmetically acceptable solvent chosen from water and a water/organic solvent mixture.

16. A ready to use hair dye composition comprising, in a cosmetically acceptable solvent:
- (a) one or more divalent metal salts of an inorganic acid chosen from metal halides, metal hydroxides, metal sulfates, metal oxides, and mixtures thereof; and wherein the divalent metal is calcium, zinc, iron, nickel, copper, silver, magnesium, strontium, barium, manganese, or cobalt;
- (b) one or more monovalent or divalent metal salts of an organic acid chosen from metal ascorbates, formates, acetates, glycolates, gluconates, lactates, mandelates, oxalates, maleates, malonates, glyoxylates, succinates, adipates, fumarates, sebacates, citrates, tartarates, malates, tricarboxylates, glutarates, glucarates, pyrrolidone carboxylates, phenolsulfonate, salicylates, their salt derivatives thereof, salts of fatty acids having at least 10 carbon atoms, and mixtures thereof;
    wherein the monovalent metal is lithium, sodium, potassium, copper, or silver; and
    wherein the divalent metal is calcium, zinc, iron, nickel, copper, silver, magnesium, strontium, barium, manganese, or cobalt;
- (c) one or more colorants chosen from oxidative dye precursors, direct dyes, pigments, and mixtures thereof; and
- (d) one or more oxidizing agents chosen from peroxides, persulfates, perborates, percarbonates, alkali metal bromates, ferricyanides, laccases, peroxidases, redox enzymes, their salts thereof, and mixtures thereof.

17. The ready to use hair dye composition of claim 16, wherein the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

18. The ready to use hair dye composition of claim 16, wherein the one or more divalent metal salts of an inorganic acid includes calcium chloride.

19. The ready to use hair dye composition of claim 16, wherein the one or more divalent metal salts of an inorganic acid are present in an amount of from above 0 wt. % to about 50 wt. %, based on the total weight of the hair coloring composition.

20. The ready to use hair dye composition of claim 16, wherein the one or more divalent metal salts of an inorganic acid are present in an amount of from about 0.4 wt. % to about 15 wt. %, based on the total weight of the ready to use hair dye composition.

21. The ready to use hair dye composition of claim 16, wherein the one or more monovalent or divalent metal salts of an organic acid are chosen from zinc lactate, zinc gluconate, zinc phenolsulfonate, zinc salicylate, zinc pyrrolidone carboxylic acid (Zinc PCA), zinc citrate, zinc ascorbate, sodium ascorbate, sodium formate, sodium gluconate, sodium glutamate, sodium glycolate, sodium glyoxylate, sodium citrate, sodium acetate, sodium lactate, sodium malate, sodium salicylate, potassium acetate, potassium citrate, potassium gluconate, potassium lactate, lithium myristate, lithium stearate, lithium gluconate, silver citrate, silver lactate, silver salicylate, their derivatives thereof, their salt derivatives thereof, and mixtures thereof.

22. The ready to use hair dye composition of claim 16, wherein the one or more divalent metal salts of an organic acid includes zinc gluconate.

23. The ready to use hair dye composition of claim 16, wherein the one or more monovalent or divalent metal salts of an organic acid are present in an amount of from above 0 wt. % to about 50 wt. % based on the total weight of the ready to use hair dye composition.

24. The ready to use hair dye composition of claim 16, wherein the one or more monovalent or divalent metal salts of an organic acid are present in an amount of from about 0.4 wt. % to about 15 wt. %, based on the total weight of the ready to use hair dye composition.

25. The ready to use hair dye composition of claim 16, wherein the composition comprises one or more divalent metal salts of an inorganic acid chosen from calcium chloride and one or more divalent metal salts of an organic acid chosen from zinc gluconate.

26. The ready to use hair dye composition of claim 16, wherein the composition is formed from the combination of:
- a color cream composition comprising the one or more colorants chosen from oxidative dye precursors, direct dyes, pigments, and mixtures thereof and the cosmetically acceptable solvent;
- the one or more divalent metal salts of an inorganic acid; and
- the one or more monovalent or divalent metal salts of an organic acid; and
- a developer composition comprising the one or more oxidizing agents chosen from one or more oxidizing agents are chosen from peroxides, persulfates, perborates, percarbonates, alkali metal bromates, ferricyanides, laccases, peroxidases, redox enzymes, their salts thereof, and mixtures thereof;
    wherein the one or more divalent metal salts of an inorganic acid and the one or more monovalent or divalent metal salts of an organic acid are provided as separate components or together as one metal salt component.

27. The ready to use hair dye composition of claim 26, wherein the weight ratio of the total amount of metal salts to the amount of the color cream composition is from about 5:1 to about 1:5.

28. The ready to use hair dye composition of claim 26, wherein the weight ratio of the total amount of metal salts to the amount of the developer composition is from about 5:0.1 to about 1:5.

29. A hair coloring composition comprising, in a cosmetically acceptable solvent:
(a) one or more divalent metal salts of an inorganic acid in an amount of greater than 1 to about 20% by weight, based on the total weight of the hair coloring composition;
   wherein the divalent metal is calcium, zinc, iron, nickel, copper, silver, magnesium, strontium, barium, manganese, or cobalt;
(b) one or more colorants chosen from oxidative dye precursors, direct dyes, pigments, and mixtures thereof.

30. The hair coloring composition of claim 29, wherein the one or more divalent metal salts of an inorganic acid are chosen from calcium chloride, calcium sulfate, calcium nitrate, calcium carbonate and hydrogen carbonate, calcium phosphate, zinc chloride, zinc sulfate, zinc nitrate, zinc carbonate and hydrogen carbonate, zinc phosphate, magnesium chloride, magnesium sulfate, magnesium nitrate, magnesium carbonate and hydrogen carbonate, magnesium phosphate, strontium chloride, strontium nitrate, barium chloride, barium nitrate, and mixtures thereof.

31. The hair coloring composition of claim 29, wherein the one or more divalent metal salts of an inorganic acid includes calcium chloride.

32. The hair coloring composition of claim 31, wherein calcium chloride is present in an amount of greater than 1 wt. % to about 6.5 wt. %, based on the total weight of the hair coloring composition.

33. The hair coloring composition of claim 32, wherein the hair coloring composition is substantially free of one or more of ammonium salt compounds, amino silicones, and cationic surfactants.

34. The hair coloring composition of claim 29, further comprising one or more oxidizing agents or capable of being mixed with an oxidizing composition comprising:
(i) one or more oxidizing agents; and (ii) a cosmetically acceptable solvent chosen from water and a water/organic solvent mixture;
   wherein the one or more oxidizing agents are chosen from peroxides, persulfates, perborates, percarbonates, alkali metal bromates, ferricyanides, laccases, peroxidases, redox enzymes, their salts thereof, and mixtures thereof.

35. A method for artificially coloring hair and/or inhibiting the artificial coloring from fading, the method comprising contacting hair with a ready to use dye composition for a sufficient period of time to achieve a desired color of the hair and/or alteration of the color of hair; wherein the ready to use dye composition is formed from the combination of the hair coloring composition of claim 1 with an oxidizing composition containing: (i) one or more oxidizing agents chosen from peroxides, urea peroxide, alkali metal bromates, ferricyanides, peroxygenated salts, perborates, percarbonates, laccases, peroxidases, redox enzymes, and mixtures thereof, and (ii) a cosmetically acceptable solvent selected from water and a water/organic solvent mixture.

36. A multi-compartment kit for altering the color of hair comprising:
(1) a first unit containing:
   (a) above 0 wt. % to about 50 wt. % of one or more divalent metal salts of an inorganic acid chosen from salts of calcium, zinc, iron, nickel, copper, silver, magnesium, strontium, barium, manganese, cobalt, and mixtures thereof;
   (b) above 0 wt. % to about 50 wt. % of one or more monovalent or divalent metal salts of an organic acid, wherein
      the one or more divalent metal salts of an organic acid are chosen from salts of calcium, zinc, iron, nickel, copper, silver, magnesium, strontium, barium, manganese, cobalt, and mixtures thereof,
      the one or more monovalent metal salts of an organic acid are chosen from salts of lithium, sodium, potassium, copper, silver, and mixtures thereof, and
      the organic acid of the one or more monovalent or divalent metal salts of an organic acid is chosen from C1 to C9 monocarboxylic or di-carboxylic acids, polycarboxylic acids, hydroxy-carboxylic acids, and fatty acids having at least 10 carbon atoms; and
   (c) one or more colorants chosen from oxidative dye precursors, direct dyes, pigments, and mixtures thereof; and
(2) a second unit containing an oxidizing composition comprising: (i) one or more oxidizing agents chosen from peroxides, persulfates, perborates, percarbonates, alkali metal bromates, ferricyanides, laccases, peroxidases, redox enzymes, their salts thereof, and mixtures thereof, and (ii) a cosmetically acceptable solvent selected from water and a water/organic solvent mixture.

37. The multi-compartment kit of claim 36 wherein the one or more divalent metal salts of an inorganic acid, the one or more monovalent or divalent metal salts of an organic acid, and the one or more colorants of the first unit are contained in one container or are each contained in three separate containers or wherein the one or more divalent metal salts of an inorganic acid and the one or more monovalent or divalent metal salts of an organic acid are contained in one container and the one or more colorants are contained in a second container.

* * * * *